United States Patent [19]

Watson et al.

[11] 4,327,741
[45] May 4, 1982

[54] DEVICE FOR MEASURING RESPIRATION VOLUME

[75] Inventors: Herman L. Watson, Perrine; Marvin A. Sackner, Miami Beach, both of Fla.

[73] Assignee: Respitrace Corporation, Ardsley, N.Y.

[21] Appl. No.: 90,615

[22] Filed: Nov. 2, 1979

[51] Int. Cl.³ .............................................. A61B 5/08
[52] U.S. Cl. ...................................... 128/728; 272/99
[58] Field of Search ..................... 128/725, 727–730; 272/99

[56] References Cited

U.S. PATENT DOCUMENTS

| | | | |
|---|---|---|---|
| 327,403 | 9/1885 | McDonnell | 128/728 |
| 821,664 | 5/1906 | Morris | 128/728 |
| 3,512,521 | 5/1970 | Jones | 128/728 |
| 3,635,214 | 1/1972 | Rand et al. | 128/727 |
| 3,777,571 | 12/1973 | Jaeger | 128/730 X |
| 3,810,461 | 5/1974 | McCormick | 128/728 |
| 3,923,043 | 12/1975 | Yanda | 128/728 |

FOREIGN PATENT DOCUMENTS

| | | | |
|---|---|---|---|
| 465298 | 4/1914 | France | 128/728 |
| 1046118 | 10/1966 | United Kingdom | 128/728 |

OTHER PUBLICATIONS

Cooper et al., "A Bag for Measuring Respiratory Volumes", The Lancet, Feb. 13, 1960, p. 369.

Primary Examiner—Lee S. Cohen
Attorney, Agent, or Firm—Hubbell, Cohen, Stiefel & Gross

[57] ABSTRACT

A device for measuring a predetermined respiratory volume comprises an elongate, air-tight flexible bag of the predetermined volume, the bag being closed at one end and open at the other; and an elongate substantially rigid tubular member extending into the bag through its open end and occupying a major portion of the length of the bag, the bag being secured at its open end to the tubular member for forming an air-tight seal between the bag and the tubular member, the portion of the tubular member extending into the bag having a plurality of distributed apertures along its length and the portion of the tubular member outside the bag having at least one opening defining a mouthpiece.

9 Claims, 7 Drawing Figures

DEVICE FOR MEASURING RESPIRATION VOLUME

BACKGROUND OF THE INVENTION

1. Field of the Invention

This invention pertains to apparatus for measuring respiration volume and to devices utilized in the calibration of such apparatus.

2. Statement of the Prior Art

Non-invasive apparatus for measuring respiration volume are known. See, for example, the apparatus disclosed in commonly owned application Ser. No. 102,408, filed Dec. 11, 1978, now U.S. Pat. No. 4,308,872 entitled Method and Apparatus for Monitoring Respiration, now abandoned, the contents of which is incorporated herein by reference in its entirety. In use, such apparatus generally requires calibration for each patient prior to use. That is, the measurements recorded on the apparatus must be calibrated against one or more initial measurements based on a known volume of expired air. Spirometers are generally used for this purpose.

While the construction details of spirometers vary widely, they generally comprise a closed chamber having inlet and outlet openings hermetically separated by a plate or the like disposed for sliding movement in the chamber. As the patient breathes into the inlet port, the plate is forced towards the outlet port. The volume of air expired by the patient is proportional to the movement of the plate. Thus, respiration volume can be measured by suitable indicia on the chamber. Alternatively, plate movement can be detected by a transducer, which then provides a signal proportional to respiration volume. The signal may be recorded, displayed as a numerical read out, or both. An exemplary spirometer is disclosed in U.S. Pat. No. 3,848,583 issued to Parr.

While spirometers provide reasonably accurate respiration volume measurements, they are unduly complex and expensive for the limited purpose of calibrating non-invasive respiration volume measuring apparatus. Indeed, their main application is for detecting respiration volume directly.

U.S. Pat. No. 3,821,950 issued to Boehringer and U.S. Pat. No. 3,810,461 issued to McCormick each discloses a flexible, air-tight bag for measuring respiration volume. The bag is provided with a mouthpiece through which the patient breathes into the bag. Thereafter, the bag is disposed on a flat surface, such as a table, and means such as a cylindrical tube is utilized to roll the bag from one end to the other such that the air trapped in the bag is forced into one end. The rolling is continued until it is apparent that the uncoiled portion of the bag is substantially filled with air. The volume of air in the bag is determined by suitable indicia on the bag.

The principal drawback of these devices is that there is a substantial possibility of "ball-valving" upon inhalation. That is, upon inhalation from the bag, the mouthpiece may become occluded by the bag as the bag collapses. As a result, air may become entrapped in the bag. Inasmuch as it is essential to accurate respiration volume measurements that the bag be completely empty before expiration, such entrapment is undesirable. Furthermore, considering that the devices disclosed in these patents are intended as disposable monitors of respiration volume, they are unduly complex insofar as they require means for preventing the escape of air through the mouthpiece after expiration is completed so that the bag can be placed on a flat surface for rolling.

U.S. Pat. No. 3,512,521 issued to Jones discloses a breath isolator disposable between the patient and a spirometer for preventing cross contamination of patients as a result of multiple use of the spirometer. The device comprises a closed chamber having an inlet opening at one end in which a mouthpiece is fitted. Inside the chamber, the mouthpiece extends into a flexible bag. The end of the chamber opposite the mouthpiece is provided with an outlet opening which communicates, via a flexible hose, with the spirometer. It will therefore be apparent that upon expiration into the mouthpiece, the bag inflates, thereby forcing an equal volume of air from the chamber through the outlet opening and into the spirometer. While the device disclosed in the patent apparently serves its intended purpose, it is unnecessarily complicated and, therefore, uneconomical as well.

SUMMARY OF THE INVENTION

We have developed a simple, economical device which is particularly suited for calibrating non-invasive respiration volume measuring apparatus. The device has other applications as well, some of which will be discuseed hereinafter.

The device comprises an elongate, air-tight bag having a predetermined volume, and an elongate tubular member defining a bore. The bag is closed at one end and open at the other end, and the tubular member extends into the bag through its open end which is secured to the tubular member to form an air-tight seal between the bag and the tube. The portion of the tubular member extending into the bag preferably occupies a major portion of the length of the bag and has a plurality of apertures distributed along its length. The portion of the tubular member outside the bag includes at least one opening communicating with the bore for defining a mouthpiece. The mouthpiece opening preferably comprises the open end of the tubular member.

In use, the patient is instructed to inhale through the mouthpiece until the bag is completely empty as indicated by collapse of the bag about the tubular member. The patient is then instructed to exhale into the bag until the bag is full. This may be indicated visually, tactilely, or both. Once the bag is full, it is known that the patient has expired a volume of air equal to the volume capacity of the bag. Using this information, the reading recorded on the non-invasive respiration volume measuring apparatus may be calibrated.

It will be apparent that accurate calibration depends on the bag being fully devoid of air before the patient expires into the bag. This is assured by the construction of the device of the invention. Thus, it will be apparent that collapse of the bag in such a manner as to occlude the air passages between the bag and the mouthpiece is effectively precluded by the fact that the portion of the tubular member extending into the bag is provided with a plurality of apertures which provide a multiplicity of air passages, and also by the fact that the tubular member occupies a major portion of the length of the bag thereby limiting the extent to which the bag can collapse. In a modified embodiment, rings are disposed about the portion of the tubular member extending into the bag thereby further limiting the possibility of the bag collapsing about the tubular member and occluding the apertures. Still further embodiments are discussed hereinafter.

The device of the present invention may also be used as a monitor of tidal volume. This requires providing a plurality of devices having bags of different known volume capacities. The patient breathes into successively larger bags until a size is reached which the patient is unable to fill. The person administering the test then knows that the patient's tidal volume is between the volume capacities of the last bag the patient was able to fill, and the final bag, which he was unable to fill. The device may also be utilized in incentive spirometry for weaning patients off respirators and in treating the hyperventilation syndrome. The use of the device in these applications will be described in greater detail hereinafter.

To the extent applications of the device of the invention require bags having different volume capacities, an alternative is to dispose the bag portion of the device in a closed chamber having a known volume smaller than the volume capacity of the bag. The patient may then be instructed to breathe into the bag until the bag occupies substantially the entire chamber at which point it is known that the volume of air expired by the patient is substantially equal to the volume of the chamber.

The device of the invention may also be used in connection with aerosol therapy. For this application, the device is modified by providing an additional opening adjacent the mouthpiece opening. The nebulizer is connected to this opening via a tube, and a valve on the nebulizer regluates outflow therefrom. During expiration into the bag, the valve is opened and the medication, such as a bronchodilator, is mixed with the air in the bag. When the patient inhales, the valve is closed, and the patient inhales the air-bronchodilator mixture in the bag. This arrangement is more efficient than conventional aerosol therapy wherein the high velocity spray directly from the nebulizer is directed into the patient's mouth as a result of which a substantial portion of the medication is lost by deposition on the posterior pharynx.

The device of the invention may also be incorporated in a conventional spirometer to serve as a breath isolator for preventing cross contamination of microorganisms from the breath between patients. In this application, the bag is disposed in the spirometer with the mouthpiece portion of the device extending through the usual inlet opening of the spirometer. The modified spirometer is operated in the usual manner, with the patient expiring through the inlet opening. The resulting expansion of the bag displaces an equal volume of air in the chamber thereby causing movement of the usual plate or bellows towards the outlet opening, whereupon the volume of air expired by the patient may be conventionally determined. In connection with this application, it is contemplated that the device of the invention will be retrofitted on existing spirometers.

Further features, advantages and applications of the device of the present invention will be more fully apparent from the following detailed description and annexed drawings of the preferred embodiments thereof.

BRIEF DESCRIPTION OF THE DRAWINGS

In the drawings, wherein like reference numerals represent like parts.

DETAILED DESCRIPTION OF THE PREFERRED EMBODIMENTS

Figure 1:
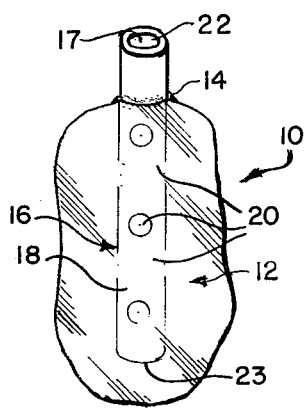
FIG. 1 is a perspective view of a preferred embodiment of a device in accordance with the present invention.

Referring now to the drawings, and initially to FIG. 1 thereof, one embodiment of a device 10 in accordance with the present invention is shown. Device 10 includes an air-impervious, flexible bag 12 open at one end 14 and an elongate substantially rigid tubular member 16 defining a bore 17 which extends into the bag 12 through its open end 14.

The seal between the end 14 of the bag 12 and the tubular member 16 must be air-tight. The required air-tight seal may be established, for example, by using a rubber ring to pinch the end 14 of the bag 12 against tube 16. Alternatively, and as contemplated in FIG. 1, a suitable adhesive may be used. In accordance with the invention, the volume capacity of the bag 12 is known.

As shown, the portion 18 of the tubular member 16 extending inside the bag 12 preferably occupies a major portion of the length of the bag. A plurality of apertures 20 are distributed along the portion 18. The portion of the tubular member 16 extending outside the bag 12 serves as a mouthpiece, and for this purpose is preferably provided with a single opening, preferably comprising the open end 22 of the tube 16. The other end 23 of the tube 16 may be open or closed, although it is preferably open thereby serving the same purpose as the apertures 20.

Bag 12 may be comprised of any suitably flexible, air-impervious material. The bag 12 is desirably transparent, although this is not necessary. Polyester or polyolefin bags are preferred, as these materials exhibit dimensional stability with repeated use. Cardboard is presently preferred for the tubular member 16 as it displays the required rigidity and is economical as well. However, cardboard is by no means the only choice, and other suitable materials for tubular member 16, such as plastic, will readily suggest themselves to those skilled in the art.

Assuming the device 10 is utilized in the calibration of a non-invasive apparatus for measuring respiration volume, such as the apparatus disclosed in commonly owned application Ser. No. 893,023, filed Apr. 3, 1978 entitled Method and Apparatus for Monitoring Respiration, the patient is first operatively connected to such apparatus. The patient is then given the device 10 and instructed to inhale through the opening 22 until all the air in the bag 12 is inspired. Actually, the patient should be instructed to inhale for a short period after the bag 12 is fully collapsed around the tubular member 16, thereby insuring that any air in the bore 17 is also inhaled. During inhalation, it will be apparent that the entrapment of air in the bag 12 is effectively precluded. Thus, because the tubular member 16 occupies a major portion of the length of the bag 12 and includes a multiplicity of apertures 20, there is little if any possibility that a portion of the bag 12 will become isolated from all the apertures 20 as a result of the collapse of the bag 12 which accompanies inhalation.

After it is determined that the patient has inspired all the air from the bag 12, the patient is next instructed to exhale into the opening 22 until the bag 12 is completely filled. This may be indicated either tactilely or visually, or both. When the bag is full, it is known that the patient has expired a volume of air equal to the volume capacity of the bag, 1.5 liters for example. Based on this, the reading recorded on the non-invasive apparatus may be calibrated. In some such apparatus, such as the apparatus disclosed in said application Ser. No. 102,408, calibration is required for two positions of the patient. In such event, the procedure described above is simply repeated for a different patient position. For example, the first calibration procedure may be carried out with the patient in the sitting position and the second calibration carried out with the patient in the supine position.

Using a bag 12 having a 1.5 liter capacity, the device 10 was tested on ten subjects. By utilizing simultaneous spirometry, it was found that after the subject tactilely sensed, without direct observation, that the bag 12 was full, the actual volume of air expired by each subject was 1.5 liters ± 1.5%.

Figure 2:
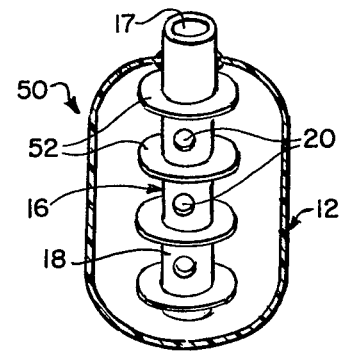
FIG. 2 is a view similar to FIG. 1, but with the bag shown in section, illustrating another preferred embodiment of a device in accordance with the present invention.

Referring now to FIG. 2, a modified device 50 in accordance with the present invention is illustrated. The device 50 is in all respects identical to the device 10 of FIG. 1, except for the fact that a plurality of rings 52 are spaced along the portion 18 of the tubular member 16. The rings prevent the bag 12 from collapsing into the holes 20 upon inhalation, which could lead to occlusion of the bore 17 and the entrapment of air in the bag 12. Like the tubular member 16, rings 52 may comprise any substantially rigid material, such as cardboard, plastic or a suitably rigid rubber. The rings 52 are preferably separately formed and slid over the tube 16 before the bag 12 is attached. They may be held in place on the tube 16 by a friction fit, an adhesive, or other well known means. Alternatively, the rings 52 may be integrally formed with the tube.

Figure 3:
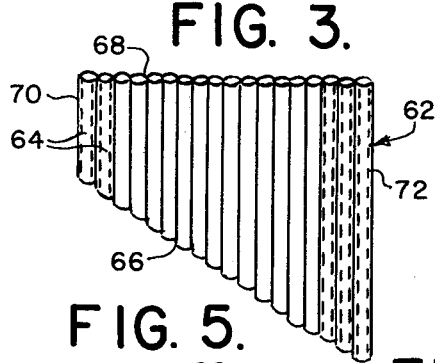
FIG. 3 is a perspective view of a piece of corrugated cardboard dimensioned for forming an elongate tubular member for incorporation in the device of the present invention.
Figure 4:
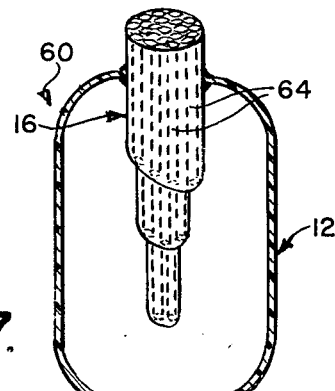
FIG. 4 is a perspective view similar to FIG. 2 showing yet another preferred embodiment of a device in accordance with the present invention and incorporating a tubular member formed from the piece of corrugated cardboard illustrated in FIG. 3.

Referring now to FIGS. 3 and 4, yet another embodiment of a device in accordance with the present invention is shown. Referring to FIG. 3, the tubular member 16 of the device 60 is formed from a foldable material 62 having a multiplicity of longitudinally extending open ended bores 64. It is presently contemplated that the material 62 will comprise corrugated cardboard. As shown, the lower edge 66 of the piece of material 62 is angled with respect to its upper edge 68.

The tubular member 16 is formed by rolling the piece of material 62 from its longer vertically extending edge 72 towards its shorter vertically extending edge 70. The tube 16 is then secured in its rolled position (FIG. 4) as by a suitable adhesive applied to the edge 72. Following the procedure described above in connection with FIG. 1, the bag 12 is then secured to the tube 16 whereupon the device 60 is ready for use.

It will be apparent that the mouthpiece of the device 60 is collectively formed by the upper open ends of the longitudinally extending bores 64 thereby giving the mouthpiece a honeycomb appearance. It will also be apparent that the lower open ends of the bores 64 terminate at different points along the length of the portion 18 of the member 16, thereby serving in the same fashion as the distributed apertures 20 in the embodiments of FIGS. 1 and 2.

Thus far, the sole application suggested for the devices of FIGS. 1-4 has been for calibrating non-invasive respiration volume measuring apparatus. There are, however, other applications. While some of these other possible applications will now be described in connection with the device 10 of FIG. 1, it should be understood that any of the devices of FIGS. 1-4 may be used.

One possible application for the device 10 of FIG. 1 is as an approximate monitor of tidal volume. Normal patients exhibit a tidal volume in the range of 300 ml–500 ml. By providing a plurality of devices 10 with bags 12 having different volume capacities, the patient breathes into successively larger bags, until a bag size is reached which the patient is unable to fill. The person administering the test would then be able to estimate the patient's tidal volume as being somewhere between the volume capacities of the last bag the patient was able to fill and the final bag, which he was unable to fill. The bags 12 could be provided, for example, in 100 ml steps, starting with a bag having a 100 ml capacity. When using the device 10 to measure tidal volume on unconcious patients, it may be preferable to reverse this procedure, i.e. have the patient first breathe into a device 10 with a large bag and then successively smaller bags.

The device 10 may also be utilized in incentive spirometry. Often, patients on respirators are required to progressively exercise their respiratory systems preparatory to complete independence from the respirator. This is generally done by having the patient breathe increasingly greater quantities of air. Providing the device 10 with bags 12 having progressively increasing volume capacities would make the device 10 perfectly suited for this purpose. Thus, if the physician wanted the patient to breathe with a volume of 1.5 liters, he would give him a device 10 with a bag 12 having a 1.5 liter volume capacity and instruct the patient to fill it. Filling of the bag 12 would be determined in the usual manner of visual or tactile perception. The patient could then be given a device 10 having a bag 12 with a volume capacity of 2.0 liters and asked to fill that bag, etc.

Still another possible application for the device 10 is in the treatment of the hyperventilation syndrome. Thus, a time honored treatment for patients who develop anxiety and expire excessive carbon dioxide has been to have the patient rebreathe into a paper bag. However, it is difficult to achieve a good mouth seal with a paper bag, and for this reason the device 10 of FIG. 1 would be an efficient and economical substitute.

Figure 5:
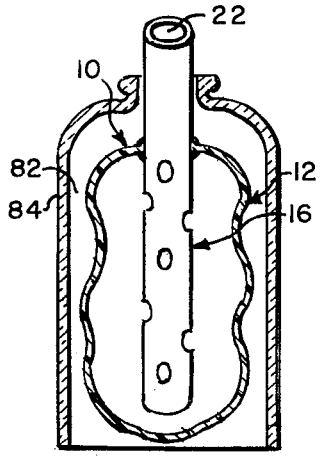
FIG. 5 is a partially perspective, partially sectional view showing the device of FIG. 1 disposed in a fixed volume chamber.

Several of the applications described thus far require that the device 10 be manufactured with bags 12 having different volume capacities. As an alternative, the effective volume of the device 10 may be reduced by disposing the device in a fixed volume chamber. For example, referring to FIG. 5, the device 10 of FIG. 1 is shown disposed in a chamber 82 defined by a bottle 84. Assuming the full volume capacity of the bag 12 is 1.5 liters, the capacity of the chamber 82 is selected at some smaller volume, for example, 0.75 liters. In use, the patient is instructed to expire into the opening 22 until the bag 12 occupies substantially the entire chamber 82. For this purpose, the bottle 84 should be transparent. When the chamber 82 is filled, it will be apparent that the volume of air in the bag 12 will be substantially equal to the volume of the chamber 82, i.e. 0.75 liters. Of course, bottles 84 having different volume capacities may be utilized to provide a range of measurements.

The seals between the device 10 and the upper and lower ends of the bottle 84 need not be air-tight. In fact, some aperture must be provided in the bottle 84 to accommodate the displacement of air from the chamber 82 as the bag 12 expands. For example, the lower end of the bottle 84 may be left open. Since almost the entire expansion of the bag 12 takes place radially of the tube 16, it will be apparent that this will not substantially affect the accuracy of the measurement, provided the height of the chamber 82 is not substantially greater than the length of the bag 12.

Figure 6:
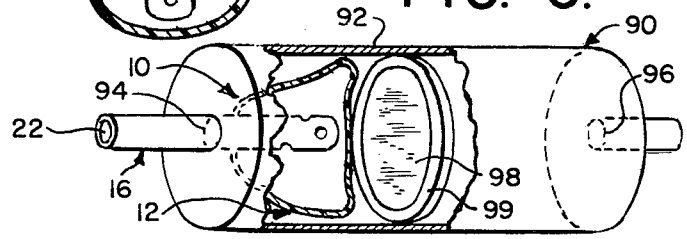
FIG. 6 is a partially broken perspective view showing the device of FIG. 1 incorporated as a breath isolator in a spirometer.

The device of the present invention may also be employed as a breath isolator in a conventional spirometer. Referring to FIG. 6, a conventional spirometer 90 comprising a cylindrical housing 92 having the usual inlet and outlet openings 94 and 96, respectively, is shown. In accordance with conventional practice, a disc-shaped plate 98 or the like is seated in the housing 92 on a rolling seal 99 such that axial sliding movement of the plate 98 is accommodated. The device 10 of FIG. 1 is disposed in the housing 92 on the inlet side of the plate 98, with the portion of the tube 16 comprising the mouthpiece extending through the inlet opening 94. The seal between the tube 16 and the opening 94 should be air-tight to prevent the escape of air from the housing 92. This may be achieved, for example, by disposing a prefitted annular member, such as a rubber ring, cork, etc. in the opening 94.

As the patient expires into the opening 22, the bag 12 will expand. The volume of air expired into the bag 12 by the patient will displace an equal volume of air in the housing 92 thereby forcing the plate 98 toward the outlet opening 96. The amount of displacement of the plate 98, which is proportional to the volume of air expired into the bag 12, may be detected in any conventional manner, as by suitable calibrations (not shown) on the housing 92 or by appropriate circuitry connected to a transducer. Whatever technique is employed, it will be apparent that the incorporation of the device 10 in the spirometer 90 effectively isolates the patient's breath from the air in the housing 92. This prevents the possibility of cross contamination when the device 90 is used on a multiplicity of patients. Assuming the spirometer 90 is used to measure tidal volume, a device 10 having a bag 12 with a volume capacity of 1.5 liters will be sufficient. Inasmuch as the volume capacity of most conventional spirometers is about 10 liters, even with the device 10 incorporated therein, the volume capacity of the spirometer will not be substantially reduced. It will be apparent that the device 10 or its equivalents may be retrofitted on practically any conventional spirometer for use in the manner described above.

Figure 7:
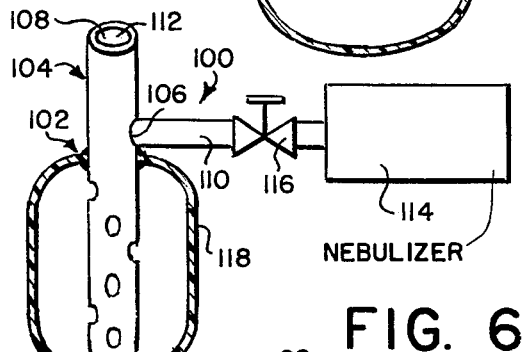
FIG. 7 is a partially perspective, partially diagrammatic, partially sectional view illustrating the device of FIG. 1 used in combination with a nebulizer for administering aerosol therapy.

The device 10 of FIG. 1 may also be used in connection with aerosol therapy. A standard way to deliver bronchodilator aerosol therapy is by directing a metered dose of the drug into the patient's mouth from a freon powered nebulizer. However, the high velocity delivery of the drug from the nebulizer results in the loss of a large portion of the drug through deposition on the mucosal surface of the posterior pharynx. The apparatus 100 illustrated in FIG. 7 is intended to overcome this problem.

As shown, the apparatus 100 includes a device 102 equivalent in all respects to the device 10 of FIG. 1 save for the fact that the tube 104 of the device 102 includes a lateral opening 106 adjacent the opening 108. One end of a tube 110 is fitted in the opening 106 for an air-tight seal with the bore 112 of the tube 104. The other end of the tube 110 is fitted on the nozzle of a conventional pressurized nebulizer 114 containing the bronchodilator. The seal between the nozzle of the nebulizer 114 and the tube 110 should also be air-tight. Alternatively, and perhaps preferably, the portion of the tube 104 outside the bag may be Y-shaped. The nebulizer would then be connected to one leg of the Y and the other leg of the Y would serve as the mouthpiece. As shown, the outflow of the bronchodilator from the nebulizer 114 is regulated by a valve 116.

In use, as the patient expires through opening 108 into the bag 118 of the device 102, the valve 116 is opened whereupon the bronchodilator from the nebulizer 114 is mixed in the bag 118 with the air expired by the patient. As the patient begins to inhale, the valve 116 is closed, and the patient inhales the bronchodilator-air mixture from the bag 118. As a result, the bronchodilator is inspired at the normal respiratory rate, thus reducing the amount of the drug that is lost through deposition on the posterior pharynx. As a result, the bronchodilator is delivered more effectively to the patient. Opening and closing of the valve 116 may be regulated manually or automatically.

While I have herein shown and described the preferred embodiments of the present invention and have suggested certain modifications thereto, it will be apparent that further changes and modifications may be made without departing from the spirit and scope of the invention. Accordingly, the above description should be construed as illustrative and not in the limiting sense, the scope of the invention being defined by the following claims.

What is claimed is:

1. A device for measuring a predetermined respiratory volume comprising:
    an elongate, air-tight, flexible bag of said predetermined volume, said bag being closed at one end and open at the other end; and
    an elongate substantially rigid tubular member defining a bore, a portion of said tubular member extending into said bag through said open end thereof, the remaining portion of said tubular member extending outside the bag, the portion of the tubular member extending inside the bag occupying a major portion of the length of the bag, said bag being secured at its open end to said tubular member and forming an air-tight seal between said bag and said tubular member, said portion of said tubular member extending into said bag having a plurality of apertures distributed along the length thereof in communication with said bore, the portion of said tubular member outside said bag having at least one opening defining a mouthpiece in communication with said bore, said plurality of apertures providing a multiplicity of air passages between said bag and said mouthpiece for preventing the entrapment of air in said bag upon inhalation through said mouthpiece.

2. The device according to claim 1, and further comprising a plurality of annular members secured to the portion of said tubular member extending into said bag for limiting the extent of collapse of said bag about said tubular member during inhalation.

3. The device according to claim 1, wherein the portion of said tubular member outside said bag is open ended and wherein said at least one opening comprises said open end of said portion.

4. The device according to claim 1, wherein the portion of the tubular member extending inside said bag is open ended.

5. The device according to claim 1, and further comprising an additional opening in the portion of said tubular member outside said bag, said additional opening being adapted for connection to a nebulizer.

6. The device according to claim 1, and further comprising a light transmissive housing defining a closed chamber having a predetermined volume less than said predetermined volume of said bag, said bag being disposed in said chamber with said mouthpiece extending outside said chamber, whereby when said bag substantially fully occupies said chamber as a result of expiration through said mouthpiece, the volume of air in said bag is approximately equal to the predetermined volume of said chamber.

7. The device according to claim 1, further comprising a housing defining a closed chamber having an inlet opening and an outlet opening; means moveable in response to the expiration of air into said chamber through said inlet opening; and means for measuring the movement of said moveable means for measuring the volume of air expired into said chamber;

said bag being disposed in said chamber with said portion of said tubular member outside said bag being received in said inlet opening and secured thereto and forming an air-tight seal between said tubular member and said housing, whereby expiration into said mouthpiece results in expansion of said bag in said chamber.

8. The device according to claim 1, further comprising a second opening also in communication with said bore;

means for connecting the output of an aerosol device to said second opening for communication with said bore; and means for unblocking the output from said aerosol device as said patient expires through said mouthpiece and blocking the output from said aerosol device as said patient inspires through said mouthpiece.

9. The device according to claim 8, wherein said portion of said tubular member outside said bag is Y-shaped, and wherein said one opening comprises the open end of one leg of said Y-shaped portion and said second opening comprises the open end of the other leg of said Y-shaped portion.

* * * * *